(12) United States Patent
Brannon

(10) Patent No.: US 8,506,475 B2
(45) Date of Patent: Aug. 13, 2013

(54) FLEXIBLE SCOPE ENDOSCOPE

(76) Inventor: James K. Brannon, Leawood, KS (US)

( * ) Notice: Subject to any disclaimer, the term of this patent is extended or adjusted under 35 U.S.C. 154(b) by 420 days.

(21) Appl. No.: 12/763,213

(22) Filed: Apr. 20, 2010

(65) Prior Publication Data

US 2010/0268024 A1    Oct. 21, 2010

Related U.S. Application Data

(60) Continuation-in-part of application No. 12/706,706, filed on Feb. 16, 2010, now abandoned, which is a continuation-in-part of application No. 10/928,553, filed on Aug. 26, 2004, now Pat. No. 7,445,595, which is a division of application No. 09/957,817, filed on Sep. 19, 2001, now abandoned.

(60) Provisional application No. 61/170,508, filed on Apr. 17, 2009.

(51) Int. Cl.
*A61B 1/01* (2006.01)
*A61M 5/00* (2006.01)

(52) U.S. Cl.
USPC ............................ 600/114; 600/104; 604/264

(58) Field of Classification Search
USPC .................... 600/114, 105, 104; 606/86, 89, 606/95, 96; 604/264
See application file for complete search history.

(56) References Cited

U.S. PATENT DOCUMENTS

| | | | | |
|---|---|---|---|---|
| 4,254,762 A | * | 3/1981 | Yoon | 600/114 |
| 4,765,314 A | * | 8/1988 | Kolditz et al. | 600/114 |
| 5,217,441 A | * | 6/1993 | Shichman | 604/536 |
| 5,287,845 A | * | 2/1994 | Faul et al. | 600/135 |
| 5,313,934 A | * | 5/1994 | Wiita et al. | 600/109 |
| 5,354,302 A | * | 10/1994 | Ko | 606/104 |
| 5,400,767 A | * | 3/1995 | Murdoch | 600/157 |
| 5,478,329 A | * | 12/1995 | Ternamian | 604/274 |
| 5,575,756 A | * | 11/1996 | Karasawa et al. | 600/157 |
| 5,634,911 A | * | 6/1997 | Hermann et al. | 604/256 |
| 5,941,815 A | * | 8/1999 | Chang | 600/114 |
| 6,086,530 A | * | 7/2000 | Mack | 600/121 |
| 6,315,714 B1 | * | 11/2001 | Akiba | 600/114 |
| 6,440,061 B1 | * | 8/2002 | Wenner et al. | 600/114 |
| 2002/0103420 A1 | * | 8/2002 | Coleman et al. | 600/173 |
| 2006/0020165 A1 | * | 1/2006 | Adams | 600/121 |
| 2009/0043165 A1 | * | 2/2009 | Kucklick et al. | 600/125 |
| 2010/0069716 A1 | * | 3/2010 | Chin et al. | 600/114 |

OTHER PUBLICATIONS

Smith&Nephew, Endoscopy Division 2010 Product Catalog, ClearTrac™ Flexible Disposable Cannula System, p. K14.

* cited by examiner

*Primary Examiner* — John P Leubecker
(74) *Attorney, Agent, or Firm* — Intellectual Property Center, LLC; Arthur K. Shaffer

(57) ABSTRACT

A flexible endoscope for extending between an incision and a surgical site, the flexible endoscope including an endoscopic cylinder received by an outer flexible sleeve, the endoscopic cylinder including an outer contact surface received by the flexible sleeve with a helical thread, a flanged structure associated with the flexible sleeve and corresponding to a proximate handle end of said endoscopic cylinder, and a directional guide angularly extending from said outer surface and tapered.

7 Claims, 5 Drawing Sheets

US 8,506,475 B2

FLEXIBLE SCOPE ENDOSCOPE

CROSS REFERENCE TO RELATED APPLICATION

This application is a continuation in part of U.S. Non-Provisional application Ser. No. 12/706,706 filed on Feb. 16, 2010 and is the non-provisional of U.S. Provisional Application 61/170,508 (expired) filed on Apr. 17, 2009 which was a continuation in part of U.S. patent application Ser. No. 10/928,553 filed on Aug. 24, 2004 which is a divisional of U.S. patent application Ser. No. 09/957,817, filed Sep. 19, 2011 (abandoned), the contents of which are hereby incorporated by reference.

FIELD OF THE INVENTION

This invention relates generally to endoscopic surgical instruments. Specifically, the present invention relates to a flexible endoscopic trephine which provides a moment arm for greater insertion rigidity for positioning a flexible endoscope during surgical procedures at a surgical site a method for using the same in orthopedic procedures.

BACKGROUND OF THE INVENTION

1. Field of the Invention

This invention relates to portals for endoscopic instruments and endoscopic procedures typically employing endoscopic instruments within a patient targeted towards a surgical site. Generally, endoscopes are used for diagnostic and therapeutic purposes. There are many different uses for endoscopes, and frequently the endoscope design is varied, depending on its use, to optimize the performance of the endoscope for its intended purpose. However, the present invention is directed towards endoscopes adapted to receive a flexible scope for use with flexible insertion tubes for treating patients.

Generally, during some medical procedures a flexible instrument is inserted through an incision to a surgical site through an endoscope channel having a proximate and distal end and a transmission member through which the flexible instrument is transmitted. Generally, however, the flexible instrument is subject to bending and compression during travel along the transmission member of the endoscope towards the surgical site. In conventional endoscopes, problems are presented when the endoscope is placed within the incision, the proximate end of the endoscope may be partially obstructed with neighboring material causing the flexible instrument to bend or otherwise compress after transmission through the transmission member.

Endoscopes are used to treat and observe a surgical site associated with a patient and for many other tasks. In order to access the surgical site, it may be advantageous to have varying rigidity characteristics. In many cases it is desired to have a rigid section and a flexible section to allow for treatment and receipt of the endoscope while providing flexibility for conforming to body tissue.

Some attempts to address these issues have been to provide endoscopes with varying rigidity. Others include the use of portals for receiving various surgical instruments, including an endoscope during the surgical procedure. Use of flexible, plastic disposable portals during surgical procedures have several known benefits, including the flexibility within the incision and the lower production cost, along with the savings provided by disposal of the portal. However, use of conventional disposable portals with a conventional metal endoscopes present several disadvantages. Generally, positioning the endoscope at the portal opening associated with the surgical site may present problems. For example, during retraction of the flexible instrument, the proximate end of the endoscope may damage the flexible scope, allowing portions of the flexible scope to remain at the surgical site. This is problematic.

The distance and angularly alignment associated with the proximal ends of the endoscope and the portal may present disadvantages. Particularly, with an angular or spatial misalignment, it is very difficult to transmit the flexible instrument through the endoscope to the surgical site for treatment. This difficulty is generally referred to as insertional rigidity, in that without proper insertional rigidity, the flexible instrument will have limited operational effectiveness. By spacing the proximal end of the endoscope too far from the proximal end of the portal, the flexible scope will compress or bend which will impede its use. By spacing the proximal ends too close, the flexible scope may not adequate insertional rigidity to overcome the resistance of any obstructing materials. Likewise, by angularly orientation of the proximal end of the endoscope in relation to the surgical site may limit the use of the flexible instrument during the surgical procedure. Therefore, there is a need to provide an endoscope optimally configured in association with a plastic portal for receiving and transmitting a flexible instrument from a posterior position towards an anterior position associated with a surgical site.

SUMMARY OF THE INVENTION

The present invention has been made in order to solve the previously stated problems with a combination rigid endoscope and flexible portal provide a varying rigidity endoscope for use in receiving and transmitting a flexible instrument to a surgical site.

DETAILED DESCRIPTION OF THE INVENTION

I. Introduction

Figure 1:
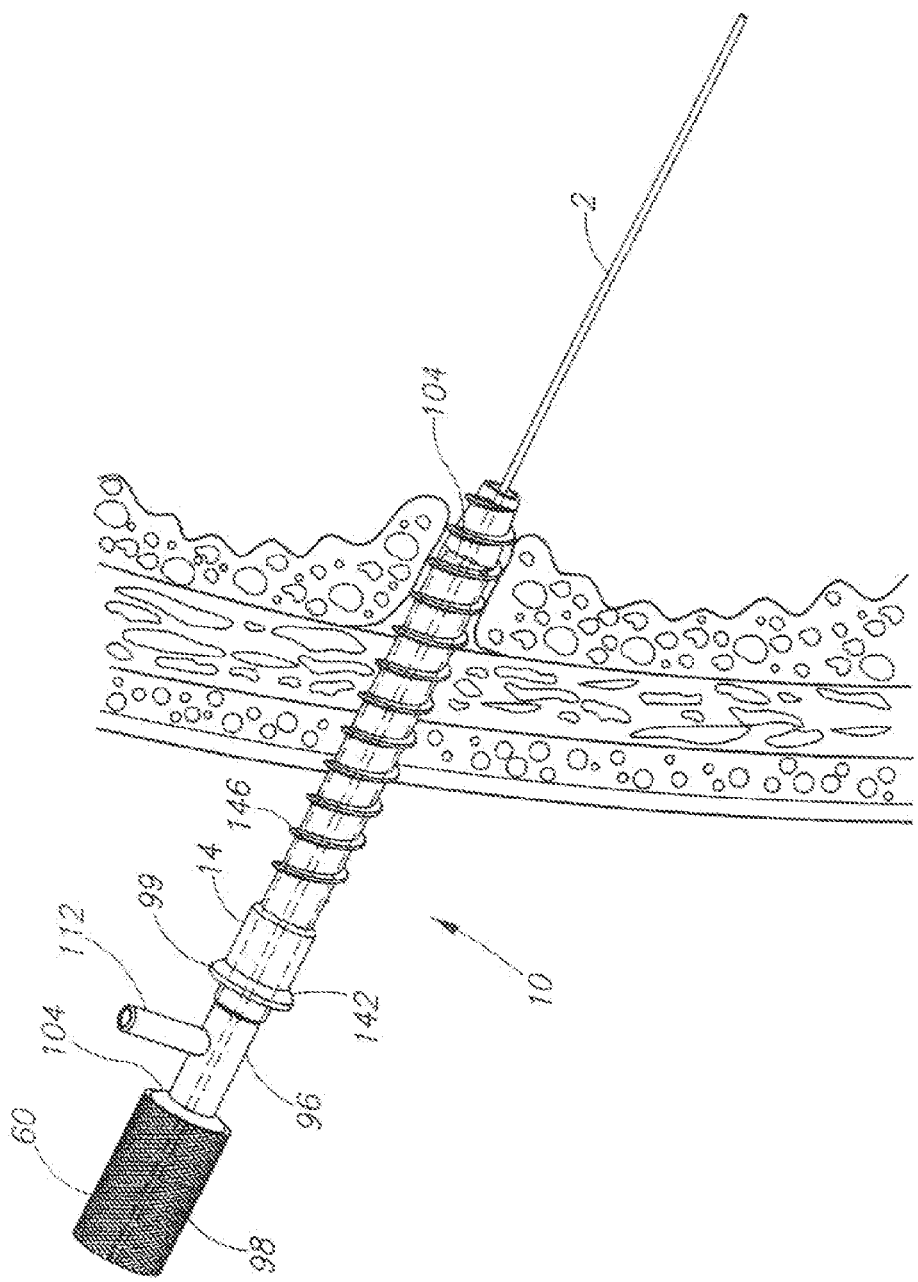
FIG. 1 is a right side perspective view of the rigid endoscope in combination with the flexible portal in receipt of a flexible instrument and associated with a cavity wall.
Figure 2:
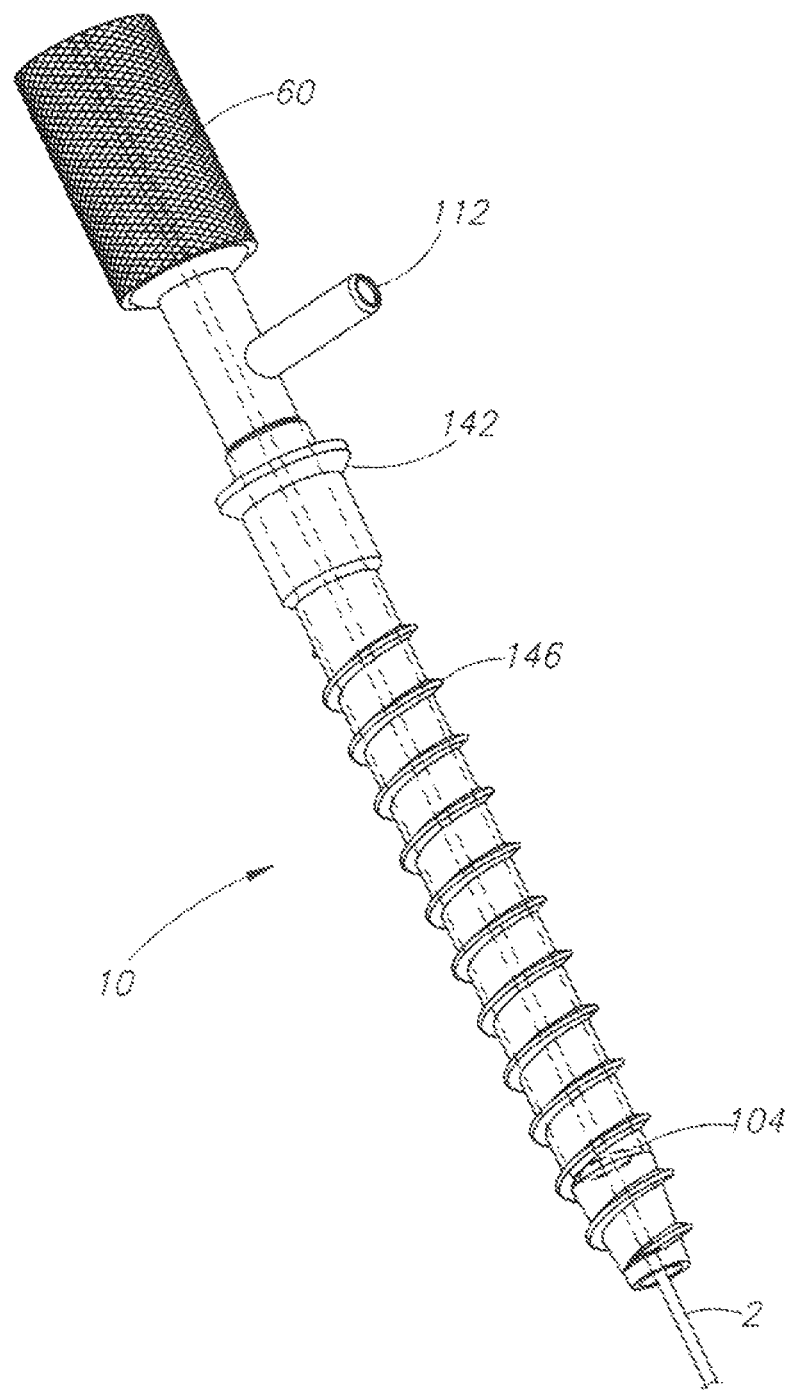
FIG. 2 is a right side perspective view of the endoscope portal combination according to FIG. 1.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

II. Rigid Endoscope in Combination with Flexible Portal

Before describing embodiments of the present invention, explanation will be provided on the basic concept of the invention.

A conventional flexible instrument is transmitted through a cylindrical tube for treatment at a surgical site. In use, the flexible instrument is controlled at a position posterior to the incision, while the anterior portion of the flexible instrument is expected to behave in like manner. However, during transmission of the flexible instrument through the cylindrical tube, there are two primary causes of degradation which impact the insertional rigidity of the flexible instrument. The first is compression or flexural rigidity caused for example by friction and the other is twisting or torsional deformation.

Flexural rigidity is best described in terms of properties that are relatively easy to measure, for example, the diameter of the flexible instrument extending through the endoscope and the elastic (Young's) modulus E of the material or materials. If the flexible instrument is comprised of a single cylindrical structure fabricated from a single material, flexibility can be defined as the inverse of the product of the moment of inertia I of the cross section with respect to the bending axis and the young's modules E. The product EI is known in scientific literatures as "flexural rigidity." For a cylindrical structure having a circular cross-section fabricated from a single material, the moment of inertia I is $\pi d^4/64$, where d is the diameter of the cylindrical structure. When the cylindrical structure has a uniform flexibility or flexural rigidity over a distance, then the flexibility can be measured more directly.

By holding one end of the uniform section fixed, applying a known weight or force perpendicular to the cylindrical structure at the other end of the uniform section, the deflection from the original straight axis will be proportional to the force or weight applied, as well as the cube of the length tested. Thus, the deflection corresponding to a known load or the force required to cause a known deflection, can be used as a direct measure of the cylindrical structure's flexibility or flexural rigidity for cases where the flexibility is uniform over a sufficient length.

Another factor impacting the flexural rigidity is frictional resistance generated between the interior surface of the endoscope and the flexible instrument. As the flexible instrument is contacts the interior surface of the transmission member, a frictional force is generated. When the flexural rigidity of the flexible instrument is small, the frictional force association with the interior surface is small as applied to the flexible instrument. When the flexural rigidity of the flexible instrument is large, the frictional force is increased.

Torsional deformation on the other hand occurs when a force is directed normal to the cylindrical structure. As the cylindrical structure is transmitted through the transmission member from the proximate end to the distal end associated with the surgical site, the cylindrical structure will angularly rotate along the transmission member. The torsional force will degrade the flexible instrument during transmission so that the rotational angle applied will not be identical to the rotational motion of the flexible instrument received at the surgical site.

To improve the insertional rigidity associated with the flexible instrument, it is desirable to decrease the accumulation of stress by the torsional deformation of the surgical instrument and decrease the frictional resistance generated between the flexible instrument and the endoscope, improving the transmission of the flexible instrument to the surgical site. Stated differently, the insertional rigidity of the flexible instrument can be improved by increasing the torsional rigidity and decreasing the flexural rigidity.

The combination rigid endoscope and flexible portal provide a varying rigidity endoscope for use in receiving and transmitting the flexible instrument to the surgical site. As depicted in FIG. 1. the combination rigid endoscope and flexible portal are generally referred to herein by reference numeral 10 in receipt of a flexible surgical instrument 2, referred to herein as a flexible instrument, flexible scope, surgical instrument, or instrument passed through an incision with the endoscope 12 having a proximate and distal end associated with an anterior and posterior surface of surgical site associated with a patient.

As illustrated the endoscope 12 generally extends cylindrically between a proximal handle end 98 associated with a handle 60 towards a distal endoscopic end 104, and including an inner visual surface 106 associated with a centrally disposed lumen and an outer contact surface 96 circumscribing the inner visual surface 106. The endoscope 12 may be fabricated from a rigid or flexible material such as polyethylene or stainless steel and is adapted for the receiving surgical instruments such as, but not limited to the flexible scope 2 illustrated in FIG. 1. Generally, the endoscope 12 facilitates extending various surgical instruments towards a surgical site which is illustrated in near the posterior surface. The endoscope 12 is also illustrated with a side opening 112 oriented normal to an endoscopic cylinder generally defined by the outer contact surface 96 and the inner visual surface 106.

The endoscopic cylinder according to the present invention includes a flexible sleeve 14, which, for example, can take the form of a cannula or portal sleeve or other structure providing a passage through a cavity wall and extends from an open proximal end 99 associated with the proximal handle end 98 towards the distal endoscopic end 104 adapted for being disposed at an internal surgical site in a body cavity. Optionally, the endoscope 12 may be utilized with an endoscopic portal 10 having an elongated sleeve presenting a central channel for receiving the endoscope 12 between an anterior surface and a posterior surface. In use, the endoscopic portal provides repeated entrance to a guided passageway between the incision to the surgical site.

Generally, the proximal handle end 98 is adapted for being disposed externally from the cavity, the lumen extending therebetween. The open proximal end 99 of sleeve 14 is illustrated as being adapted for receipt of the endoscope 12 near the proximal handle end 98 while includes a flanged structure 14a for support by the incision or cavity wall. In addition, the flexible sleeve 14 may optionally include a helical thread or other walled structures 14b for securing the flexible sleeve 14 to the cavity wall to facilitate threaded receipt, while limiting unnecessary linear motion of the flexible sleeve 14 within the cavity. While the illustrated helical thread 14b extends the length of the flexible sleeve 14, it may not be present and if present may only extend along a portion of the flexible sleeve 14, to provide sufficient structure for limiting unnecessary linear motion.

Figure 3:
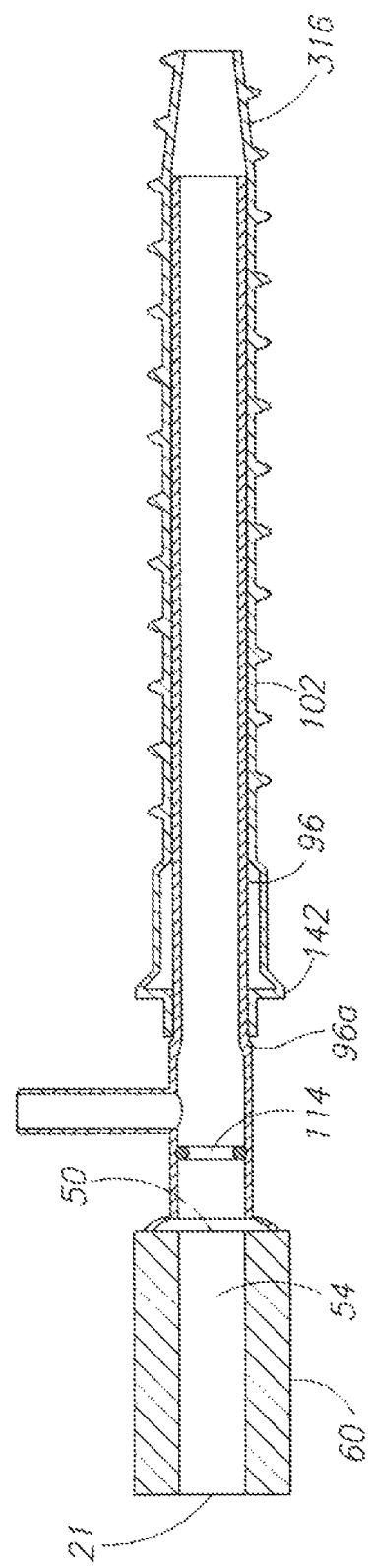
FIG. 3 is a cross section of the endoscope portal combination according to FIG. 1.
Figure 4:
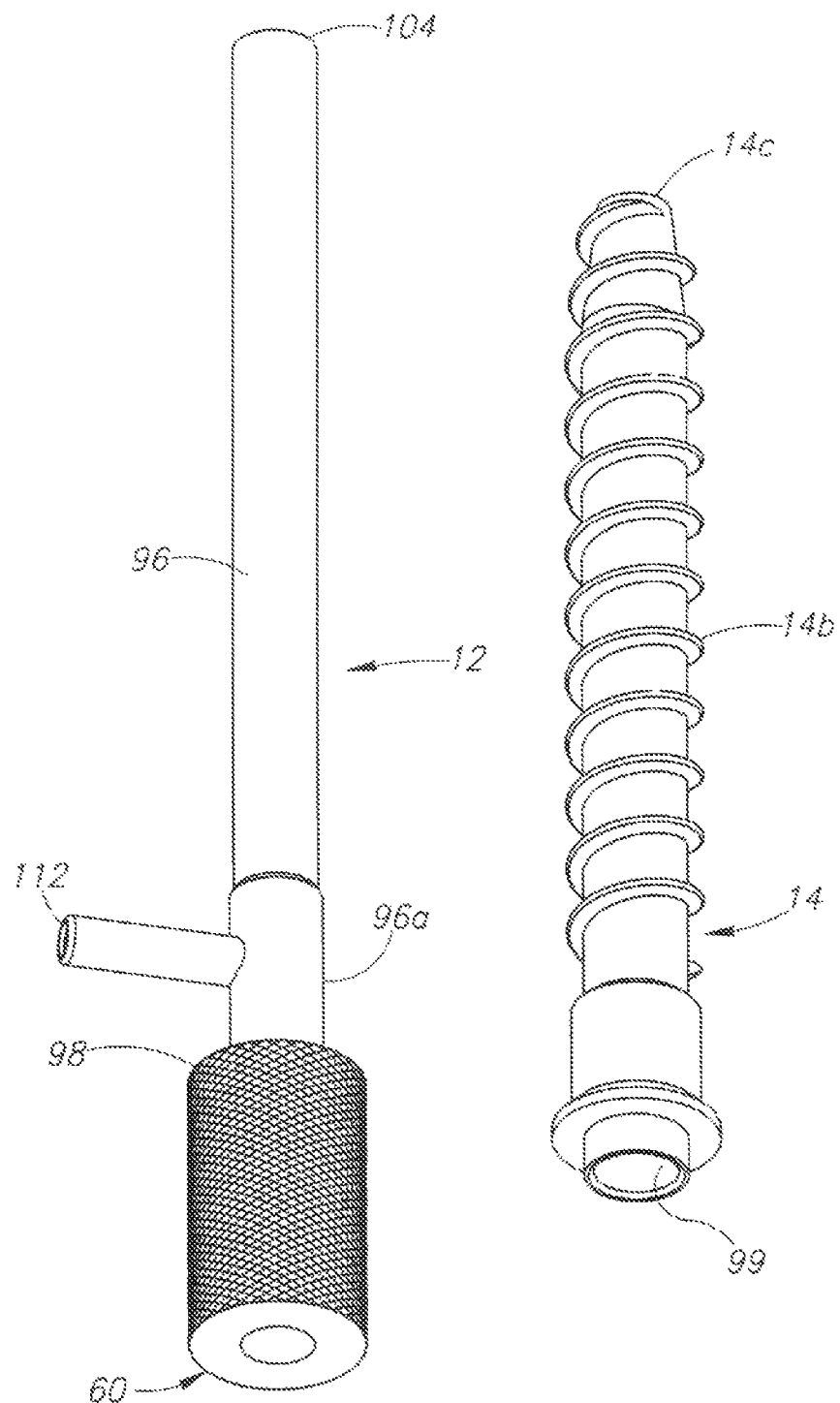
FIG. 4 is a right side bottom perspective view of the endoscope portal combination separated from each other.
Figure 5:
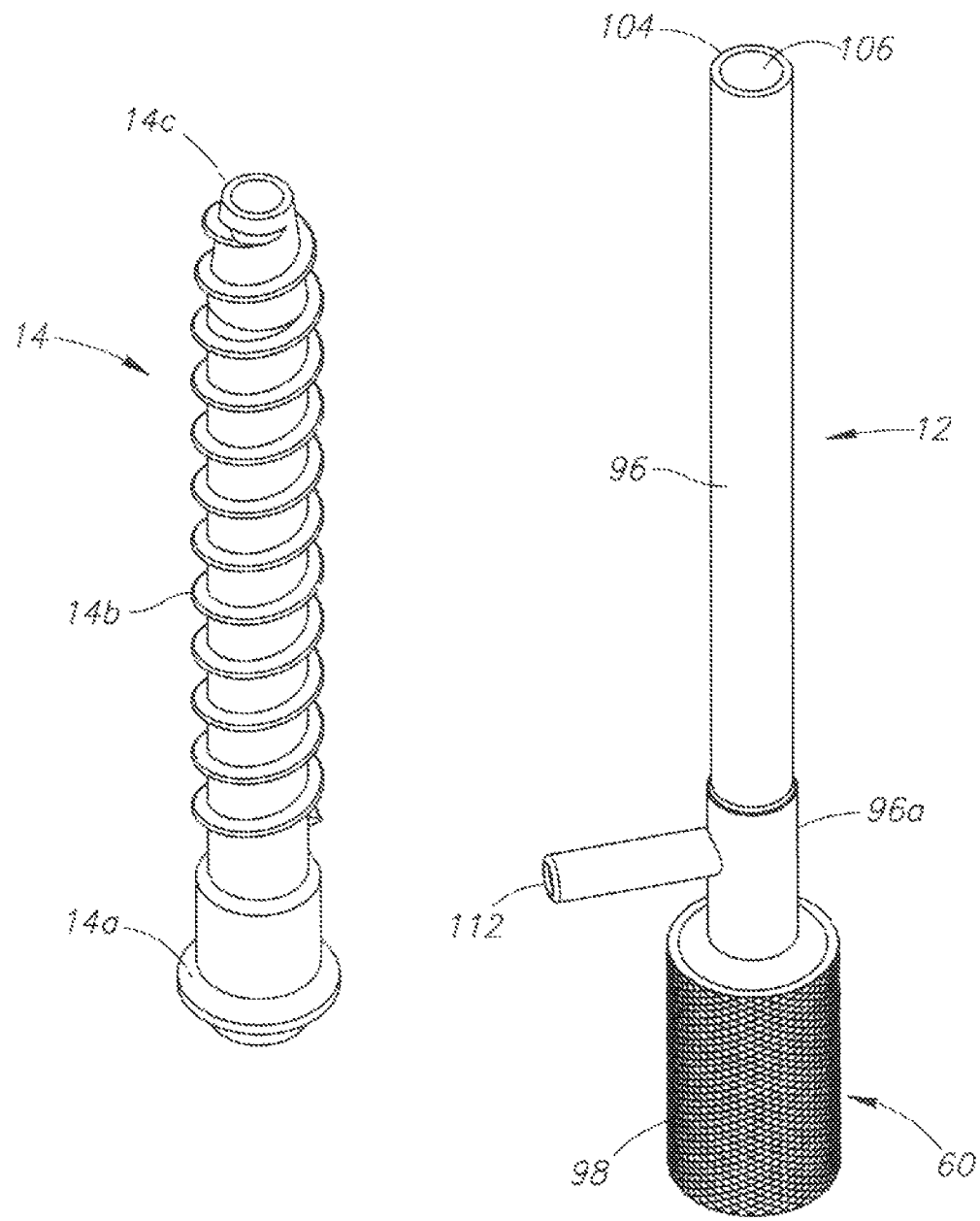
FIG. 5 is a left side bottom perspective view of the endoscope portal combination according to FIG. 4.

The flanged structure 14a as illustrated in FIG. 3, includes an outwardly tapered region extending radially from the endoscopic cylinder and adapted for compressing the cavity wall. The compressed cavity wall surface provides additional support for the flanged structure 14a whereby the flexible sleeve 14 is maintained on the outer cavity wall. The flanged structure 14a is of sufficient size and dimension to provide a hermetic seal at the juncture of the flexible sleeve 14 and the incision associated with the cavity wall.

The endoscopic cylinder includes the outer contact surface 96 of a dimension adapted to slideably receive a longitudinal surface 102 associated with the flexible sleeve 14. The outer contact surface 96 is further configured of a size, shape and dimension to establish a hermetic seal at the juncture of the sleeve 14 and the endoscope 12 along the circumferential seat 96a associated with the endoscope 12 near the proximal handle end 60. The flexible sleeve 14 is of a shape, size and dimension to receive an endoscope coaxially along the inner visual surface 106. Optionally, the flexible sleeve 14 may include a flanged structure 14b which is shown having been engaged by the outer contact surface 96. Operationally, situated about the proximal handle end 98 is the side opening 112 which supplies or removes an irrigation fluid through the endoscopic cylinder via distal endoscopic end 104 at the surgical site. The side opening 112 is preferably adapted of a size and shape to receive and transmit the irrigation fluid.

The distal endoscopic end 104 positioned within the cavity wall, is illustrated in FIG. 1 in receipt of the flexible scope or other surgical instrument 2 having been advanced into the endoscopic cylinder, substantially coaxially along the inner visual surface 106 for operation at the surgical site. The flexible instrument 2 passes into the endoscopic cylinder after first passing through the handle 60 and over a proximal stabilizing support 114.

The proximal stabilizing support 114, being of a size and dimension to allow distal and proximal advancement of the flexible instrument 2 or other surgical instruments within the endoscopic cylinder supports the received instrument 2 and generally facilitates insertional rigidity of the flexible instrument 2 through the endoscopic cylinder and the flexible sleeve 14 towards the surgical site. Depending on the position of the stabilizing support member 114 in relation to the received surgical instrument, greater or less insertional rigidity may be provided. In this way the operator may adapt the present invention for a number of desired operational settings. Generally, stabilizing support 114 supports the received surgical instrument 2, thereby, facilitating insertional rigidity of the flexible instrument 2. The stabilizing support 114 may be fabricated or coated with various materials to enhance the insertional rigidity quality of the flexible instrument 2 by decreasing the frictional surface or otherwise decreasing the flexural rigidity and increasing the torsional rigidity. The proximal stabilizing support 114 is further of a size and dimension adapted to present a seal, limiting the flow of air or fluid at the juncture thereof and the longitudinal surface of the flexible instrument 2. Additional lateral supports (not shown) may be provided within the central lumen for enhanced operational benefits including supporting the received surgical instruments 2.

The endoscopic cylinder flexible sleeve 14 combination consistent with an embodiment of the present invention, in receipt of the flexible instrument 2 allows for controlled manipulation of the flexible instrument 2 through manual manipulation of the proximate handle end 98 associated with the open proximal end 99. In this way, manipulation of one end of the surgical instrument 2 allows for surgical impact at the opposite surgical site.

The circular opening associated with the open proximal end 99 at handle end 21 is axially aligned with lumen and corresponds to the cross section of the introduced surgical instrument 2 through the endoscope 12. Handle 60 also includes a cylindrical shaft 54 extending axially from the handle end 21 to a lateral port of entry 50. The handle 60 is generally of uniform thickness and is illustrated with an optional frictional surface extending along the circumferential surface thereof for improved handling.

Generally, the distal end 104 of the endoscope 12 is separated a distance from a distal sleeve end 14c which is further separated from the surgical site. Depending upon the characteristics and configuration of the received flexible instrument 2, the separation distance is between X and Y millimeters, where a distance less than X or greater than Y would provide non-optimal insertional rigidity for the flexible instrument 2. Separating the distal sleeve end 14c and distal endoscopic end 104 between X and Y mm, may improve the insertional rigidity of the flexible instrument 2 as it is transmitted to the surgical site in relation to conventional endoscopes. The change between X and Y is represented by $\Delta x$ and the moment of inertia corresponding to the outer contact surface 96 corresponds to $mr^2$ where m is the mass of the endoscope 12 and r is the corresponding radius. The moment of inertia related to the flexible instrument 2 therefore corresponds to $(mL^2)/3$ where L is the length, $\Delta x$, and m is the mass of the flexible instrument 2. In this case, the flexible instrument 2 has an exponentially greater moment of inertia based upon $\Delta x$, however, as $\Delta x$ increases the moment decreases resulting in a corresponding loss of rigidity of the flexible instrument 2. In addition, by decreasing the $\Delta x$, cartilage or other tissue associated with the surgical site may be damaged by a corresponding increased rigidity associated with the flexible instrument 2 extending past the distal end 104. Maintaining the proper distance of $\Delta x$ between the distal end 104 and the sleeve distal end 14 reduces the probability of damage to any surrounding tissue while providing optimal insertional rigidity.

Optionally, the distal end 104 may include a non-tapered tip (not shown) to reduce physical injury at the surgical site caused by the endoscope. In some applications a sharp or tapered end may damage soft tissue associated with the surgical site. Providing a blunt, arcuate or non-tapered tip may reduce injury caused by a tapered distal end 104.

Optionally, the flexible sleeve 14 may include an improved directional surface 316 associated with the distal sleeve end 14c, adapted to reduce deformation of any transmitted flexible instrument 2 and to improve the associated insertional rigidity of the flexible instrument 2 as it travels past the distal endoscopic end 104 to the distal sleeve end 14c. As further illustrated in FIG. 3, the directional surface 316 is radially tapered outwardly from the distal endoscopic end 104. In addition, the distal sleeve end 14c may include a coating to reduce friction and for improving the insertional rigidity of the received flexible instrument 2.

An offset is presented between the flexible sleeve 14 and the endoscope 12 to promote coaxial movement of the flexible instrument 2 along the endo scope 12 through the flexible sleeve 14. As the flexible instrument 2 exists the distal end 104 of the endoscope 12 it continues traveling coaxially towards the surgical site through the flexible sleeve 14 while supported along the inner visual surface 106 associated with the endoscope 12 and the flexible sleeve 14.

FIG. 3 illustrates the sleeve 14 with outer contact surface 96 separated from the inner visual surface 106, the directional guide 316 angularly extending from the outer surface 96 towards the inner surface 106 associated with the lumen. The outer surface of the distal sleeve end 14c in association with the distal endoscopic end 104 are generally adapted for telescopic placement near the surgical site. During the transmission of the flexible instrument 2 through the endoscopic cylinder to the surgical site, the directional guide 316 biases the flexible instrument 2 towards the surgical site, longitudinally. Biasing the surgical instrument 2 longitudinally, improves the insertional rigidity of the flexible instrument 2, whereby, the surgeon has improved control for operation near the surgical site. The shape of the directional guide 316 in combination with the offset and the underlying proximal stabilizing support promotes improved insertional rigidity of the flexible instrument 2 at the surgical site.

Additionally, the flexible instrument 2 may include complementary mechanical structure for mechanically securing the surgical instrument 2 to the endoscopic cylinder at the proximal handle end 98 for securely aligning the flexible instrument 2 within the endoscope during coaxially transmission along the inner visual surface 106. While we have generally referred to the flexible instrument 2, it may be any type of surgical instrument to be dispensed to the surgical site which may benefit from improved insertional rigidity.

An alternative directional guide (not shown) may be angularly orientated to made with the received surgical instrument 2 extending through the endoscope and sleeve combination 10 via a shaft connectably secured to the instrument 2. The alternative directional guide thereby being adapted to improve insertional rigidity of received instruments through the inner visual surface 106 and longitudinal surface 102 extending the instrument 2 coaxially therealong.

While the invention has been described with respect to specific examples including presently preferred modes of carrying out the invention, those skilled in the art will appreciate that there are numerous variations and permutations of the above described systems and techniques that fall within the spirit and scope of the invention as set forth in any claims.

Having thus described the invention, what is claimed as new and desired to be secured by Letters Patent is as follows:

1. A flexible endoscope for extending between an incision and a surgical site, said flexible endoscope comprising:
    an endoscopic cylinder received by an outer flexible sleeve, said endoscopic cylinder having a outer contact surface coaxially received by the flexible sleeve, said flexible sleeve having a helical thread circumscribing substantially along an outer surface of said flexible sleeve,
    a flanged structure associated with said flexible sleeve and corresponding to a proximate handle end of said endoscopic cylinder, and
    a directional guide angularly and distally extending from said outer surface and being radially tapered from said endoscopic cylinder.

2. The endoscope according to claim 1, further comprising an internal proximal stabilizing support dimensioned to slidably receive a surgical instrument passing through said endoscope while restricting fluid flow at the juncture of said proximal stabilizing support and said surgical instrument, whereby the surgical instrument can be manipulated to a surgical site.

3. The endoscope according to claim 2, wherein said proximal stabilizing support is located between the endoscopic cylinder and a handle of said endoscope.

4. The device according to claim 1 wherein said outer contact surface of said endoscopic cylinder and an inner surface of the flexible sleeve presents a hermetic seal at a juncture thereof.

5. The endoscope according to claim 1 wherein said endoscopic cylinder further comprises a side opening associated with said proximate handle end spaced from a distal endoscopic end, said side opening in fluid communication with said distal endoscopic end.

6. The endoscope according to claim 5, further comprising a lateral support dimensioned to slidably receive a surgical instrument while restricting fluid flow at the juncture of said lateral support and said surgical instrument, whereby said lateral support is located between said side opening and said distal endoscopic end and a proximal stabilizing support is located between said proximate handle end and said side opening.

7. The device according to claim 1, wherein said directional guide is configured to bias a surgical instrument towards said surgical site.

* * * * *